(12) United States Patent
Nagai

(10) Patent No.: US 7,477,363 B2
(45) Date of Patent: Jan. 13, 2009

(54) FLOW CYTOMETER

(75) Inventor: Yutaka Nagai, Tokyo (JP)

(73) Assignee: Nihon Kohden Corporation, Tokyo (JP)

( * ) Notice: Subject to any disclaimer, the term of this patent is extended or adjusted under 35 U.S.C. 154(b) by 240 days.

(21) Appl. No.: 11/101,547

(22) Filed: Apr. 8, 2005

(65) Prior Publication Data

US 2005/0225745 A1 Oct. 13, 2005

(30) Foreign Application Priority Data

Apr. 8, 2004 (JP) ............................ P2004-113971
Feb. 16, 2005 (JP) ............................ P2005-039264

(51) Int. Cl.
*G01N 21/00* (2006.01)
(52) U.S. Cl. ........................... 356/73; 356/340; 356/318
(58) Field of Classification Search ................. 356/340, 356/73, 318
See application file for complete search history.

(56) References Cited

U.S. PATENT DOCUMENTS

| | | | | |
|---|---|---|---|---|
| 4,273,433 A | * | 6/1981 | Norris ......................... | 396/338 |
| 4,284,412 A | * | 8/1981 | Hansen et al. ............. | 435/7.24 |
| 4,341,471 A | * | 7/1982 | Hogg et al. .................. | 356/343 |
| 4,341,993 A | * | 7/1982 | Brunsting et al. ............. | 377/10 |
| 4,523,841 A | * | 6/1985 | Brunsting et al. ............. | 356/73 |
| 5,260,764 A | * | 11/1993 | Fukuda et al. ................ | 356/73 |
| 5,367,474 A | * | 11/1994 | Auer et al. .................... | 702/21 |
| 5,928,949 A | * | 7/1999 | Sakata et al. .................. | 436/17 |
| 6,084,670 A | | 7/2000 | Yamazaki et al. | |
| 6,139,800 A | * | 10/2000 | Chandler .................. | 422/82.08 |
| 6,157,500 A | | 12/2000 | Yamazaki et al. | |
| 6,409,141 B1 | | 6/2002 | Yamazaki et al. | |
| 7,069,191 B1 | * | 6/2006 | Moore ......................... | 702/191 |
| 7,106,442 B2 | * | 9/2006 | Silcott et al. ................. | 356/338 |
| 2003/0190628 A1 | * | 10/2003 | Nakao et al. .................... | 435/6 |
| 2003/0207331 A1 | * | 11/2003 | Wilson et al. ................ | 435/7.1 |
| 2005/0029448 A1 | * | 2/2005 | Chang et al. ................. | 250/292 |
| 2005/0030519 A1 | * | 2/2005 | Roth .......................... | 356/28.5 |
| 2005/0073686 A1 | * | 4/2005 | Roth et al. ................... | 356/436 |
| 2005/0162648 A1 | * | 7/2005 | Auer et al. ................... | 356/318 |

FOREIGN PATENT DOCUMENTS

| | | |
|---|---|---|
| JP | 3-233344 A | 10/1991 |
| JP | 11-23447 A | 1/1999 |
| JP | 3350775 B2 | 9/2002 |

* cited by examiner

*Primary Examiner*—Kara E Geisel
(74) *Attorney, Agent, or Firm*—Sughrue Mion, PLLC (57) ABSTRACT

A laser light source emits a first light beam irradiating a solution including target particles and being flowed in a flow cell to generate forward scattered light and orthogonal scattered light therefrom. A light emitting diode emits a second light beam irradiating the solution in the flow cell to generate at least one wavelength of fluorescence therefrom. A first detector is adapted to detect the forward scattered light. A second detector is adapted to detect the orthogonal scattered light. At least one third detector is adapted to detect the at least one fluorescence. A first filter is disposed between the flow cell and the third detector and adapted to eliminate scattered light generated from the target particles by the irradiation of the first light beam.

13 Claims, 12 Drawing Sheets

FLOW CYTOMETER

BACKGROUND OF THE INVENTION

The invention relates to a flow cytometer which radiates a laser beam toward a flow of aqueous solution containing cells, chromosomes, and biopolymers included therein, thereby detecting fluorescence and scattered light radiated from the cells or the like, to thus classify and count the number of the same.

Flow cytometers have been in wide use: (1) for measuring relative amounts, between cells, of DNA, RNA, enzyme, protein, and the like; (2) for examining functions, such as cell activity, antibody productivity, and enzyme activity; and (3) for automatically classifying types of cells, chromosomes, lymphocytes, or the like.

A conventional example of a flow cytometer of this type has the following configuration. A sample solution is prepared by, for instance, diluting and staining a blood sample. The sample solution is supplied in a form of a narrow flow to a center section of a flow cell. The narrow flow is irradiated with narrowly-converged light emitted from a light source, thereby forming a detection section. Every time a blood cell passes through the detection section, changes in scattered light and fluorescence are detected by a photodetector. A two-dimensional scattergram, wherein a scattered light intensity and a fluorescence intensity form two axes, is produced on the basis of the thus-detected signals. Demarcation lines are set on the two-dimensional scattergram, whereupon classification and counting of the particles are performed.

Figure 3:
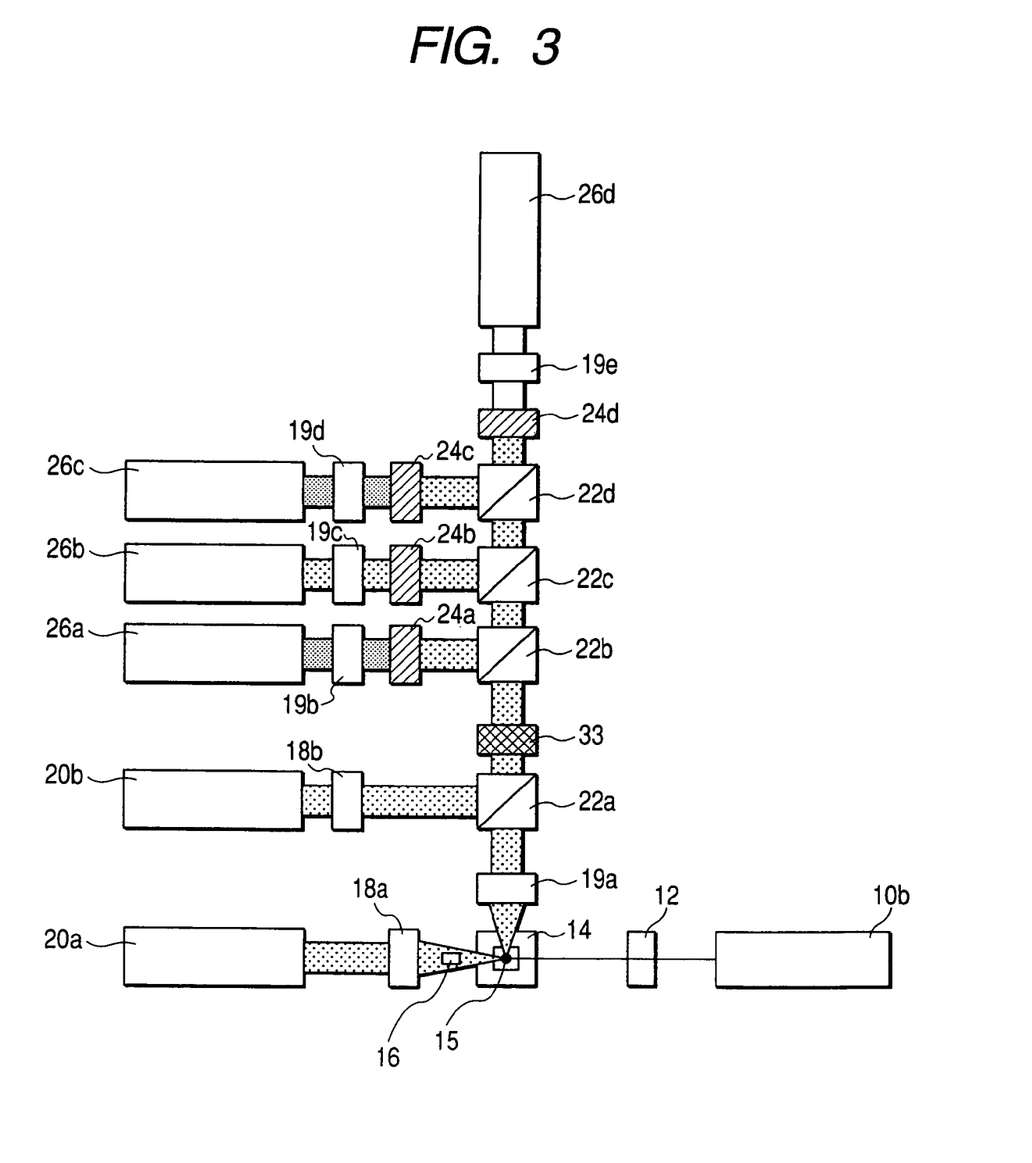
FIG. 3 is a schematic plan view of a related-art flow cytometer.

FIG. 3 shows such a flow cytometer comprising a laser light source 10b which is used for exciting both of scattered light and fluorescence. A laser beam emitted from the laser light source 10b is radiated at a target particle to be measured (hereinafter referred to as a target particle) 15 in a flow cell 14 by way of a beam shaping lens 12. As described above, the laser beam radiated at the target particle 15 excites forward scattered light, orthogonal scattered light, and fluorescence, respectively. Meanwhile, the flow cytometer is configured sum that a direct beam of the laser beam radiated toward the flow cell 14 is blocked by a shade 16 disposed in front of the flow cell 14.

As described above, forward scattered light resulting from excitation of the target particle 15 is condensed by a condenser lens 18a, input to a forward scattered light detector 20a, and converted into an electric signal. Meanwhile, the orthogonal scattered light and fluorescence having been excited on the target particle 15 are condensed by a condenser lens 19a, and brought incident to serially-arranged beam splitters 22a, 22b, 22c, and 22d in sequence.

The orthogonal scattered light is reflected by the beam splitter 22a. The thus-reflected optical beam is condensed by a lens 18b, input to an orthogonal scattered light detector 20b, and converted into an electric signal. The optical beam transmitted through the beam splitter 22a is subjected to elimination of scattered light wavelength originating from the light source for scattered light excitation or the same originating from the light source for exciting fluorescence by a wavelength filter 33, and thereafter caused to enter the serially-arranged beam splitters 22b, 22c, and 22d in sequence. A first fluorescence having been set in advance is reflected by the beam splitter 22b. The reflected light beam is condensed by a condenser lens 19b by way of a wavelength filter 24a, input to a fluorescence detector 26a, and converted into an electrical signal. Similarly, a second fluorescence having been set in advance is reflected by the beam splitter 22c. The reflected light beam is condensed by a condenser lens 19c by way of a wavelength filter 24b, input to a fluorescence detector 26b, and converted into an electrical signal. In addition, a third fluorescence having been set in advance is reflected by the beam splitter 22d. The reflected light beam is condensed by a condenser lens 19d by way of a wavelength filter 24c, input to a fluorescence detector 26c, and converted into an electrical signal. Meanwhile, a transmitted light beam is constituted of a fourth fluorescence having been transmitted through the beam splitter 22d. The transmitted light beam is condensed by a condenser lens 19e by way of a wavelength filter 24d, input to a fluorescence detector 26d, and converted into an electrical signal.

According to the flow cytometer of the above configuration, target particles are classified into the respective types of fluorescence as described above, and subjected to measurement; whereby the specific properties of the variety of target particles can be analyzed.

In such a flow cytometer, however, an argon laser is used as a light source for exciting fluorescence of a target particle. The argon laser is used because light of relatively shorter wavelength and in a blue-light region must be used as an excitation light for causing the target particle to emit fluorescence. However, an argon laser is expensive. In addition, not only is the footprint of the laser apparatus per se large, but also accompanying peripheral devices, such as a required power source for driving the laser, and the like, are also large. Furthermore, overall power consumption by the argon laser is also large.

In addition, when target particles differ, types of fluorescence to be analyzed differ. Accordingly, setting of sensitivities and threshold values of the respective detectors must be optimized by, for instance, changing settings of the wavelength filters. The operations to perform such changing are considerably complicated. Therefore, for conducting analysis of a variety of target particles, the following method would be easy and convenient. That is, target particles are specified in advance; and, on the basis thereof, a plurality of flow cytometers, in which sensitivities and threshold values for the respective wavelength filters are optimized, are installed. However, of a flow cytometer, a light source and peripheral equipment thereof are expensive. Accordingly, installation of a flow cytometer for each type of the target particles involves enormous installation cost and an enormous footprint, which is economically disadvantageous.

SUMMARY OF THE INVENTION

It is therefore an object of the invention to provide a flow cytometer which is capable of analyzing especially fluorescence of a target particle more appropriately and efficiently.

In order to achieve the above object, according to the invention, there is provided a flow cytometer, comprising:

a laser light source, which emits a first light beam irradiating a solution including target particles and being flowed in a flow cell to generate forward scattered light and orthogonal scattered light therefrom;

a light emitting diode, which emits a second light beam irradiating the solution in the flow cell to generate at least one wavelength of fluorescence therefrom;

a first detector, adapted to detect the forward scattered light;

a second detector, adapted to detect the orthogonal scattered light;

at least one third detector, adapted to detect the at least one wavelength of fluorescence;

a first filter, disposed between the flow cell and the third detector and adapted to eliminate scattered light generated from the target particles by the irradiation of the first light beam.

With the above configuration, since an inexpensive conventional laser light source may be used for exciting the forward scattered light and the orthogonal scattered light, an inexpensive flow cytometer can be obtained. In addition, since the light source for exciting the fluorescence is individually provided, the analysis for the fluorescence of the target particles can be reliably and efficiently performed.

Preferably, the flow cytometer further comprises: a condenser lens; and a first beam splitter. The laser light source and the light emitting diode are so arranged that the orthogonal scattered light and the fluorescence are incident on the condenser lens The orthogonal scattered light and the fluorescence passed through the condenser lens are divided by the first beam splitter and respectively directed to the second detector and the third detector.

With this configuration, the orthogonal scattered light and the fluorescence can be simultaneously detected with an efficient optical arrangement.

Here, it is preferable that: a plurality of third detectors, each of which includes a filter adapted to pass light having a wavelength corresponding to one of plural wavelengths of fluorescences, are provided; and the flow cytometer further comprises a second beam splitter adapted to divide the fluorescences passed through the first filter and directs each of the divided fluorescences to one of the third detectors.

With the above configuration, the scattered light generated by the irradiation of the first light beam can be collectively eliminated upon detecting the respective fluorescences.

Preferably, the flow cytometer further comprises: a second filter, disposed between the flow cell and the first detector and adapted to eliminate scattered light generated from the target particles by the irradiation of the second light beam; and a third filter, disposed between the flow cell and the second detector and adapted to eliminate scattered light generated from the target particles by the irradiation of the second light beam.

With this configuration, the forward scattered light and the second scattered light can be reliably detected.

According to the invention, there is also provided a flow cytometer, comprising:

a light source, which emits a light beam irradiating a solution including target particles and being flowed in a flow cell to generate forward scattered light, orthogonal scattered light and at least one wavelength of fluorescence;

a first detector, adapted to detect the forward scattered light;

a second detector, adapted to detect the orthogonal scattered light;

at least one third detector, adapted to detect the at least one wavelength of fluorescence; and a first composite lens, having a plurality of focal points, wherein:

the laser light source is so arranged that the orthogonal scattered light and the fluorescence are incident on the first composite lens; and the second detector and the third detector are arranged at the respective focal points of the first composite lens.

With this configuration, the sensitivity and the S/N ratio of the fluorescence detection can be enhanced.

Preferably, the light source includes a laser light source which emits a first light beam for generating the forward scattered light and the orthogonal scattered light, and a light emitting diode which emits a second light beam for generating the at least one wavelength of fluorescence.

Preferably, a plurality of lens elements, each of which has one of the focal points, are concentrically combined to form the first composite lens having a circular shape.

Alternatively, a plurality of semicircular lens elements, each of which has one of the focal points, are combined to form the first composite lens having a circular shape.

Preferably, a plurality of third detectors, each of which includes a filter adapted to pass light having a wavelength corresponding to one of plural wavelengths of fluorescences, are provided. The flow cytometer further comprises a second composite lens having a plurality of focal points and arranged at an opposite side of the flow cell to the first composite lens. The third detectors are arranged at the respective focal points of the second composite lens.

Here, it is preferable that at least one of the first composite lens and the second composite lens is formed with a pinhole at a center portion thereof.

It is also preferable that the flow cytometer further comprises an optical system including a pair of collimators, a condenser lens and a member formed with a pinhole which are arranged between the collimators. The optical system is arranged between the flow cell and at least one of the first composite lens and the second composite lens.

With the above configurations, stray light can be efficiently eliminated, thereby further enhancing the sensitivity and the S/N ratio of the fluorescence detection.

Preferably, the flow cytometer further comprises a fourth detector, adapted to measure light absorbance of the target particles.

With this configuration, in addition to the above function, the amount of light absorbing substance in the cell (particle) can be measured.

BRIEF DESCRIPTION OF THE DRAWINGS

The above objects and advantages of the present invention will become more apparent by describing in detail preferred exemplary embodiments thereof with reference to the accompanying drawings, wherein.

DETAILED DESCRIPTION OF THE INVENTION

Embodiments of a flow cytometer according to the present invention will be described in detail below with reference to the accompanying drawings. Meanwhile, for the sake of simple explanation, elements identical with those in the flow cytometer shown in FIG. 3 are denoted by the same reference numerals.

Figure 1:
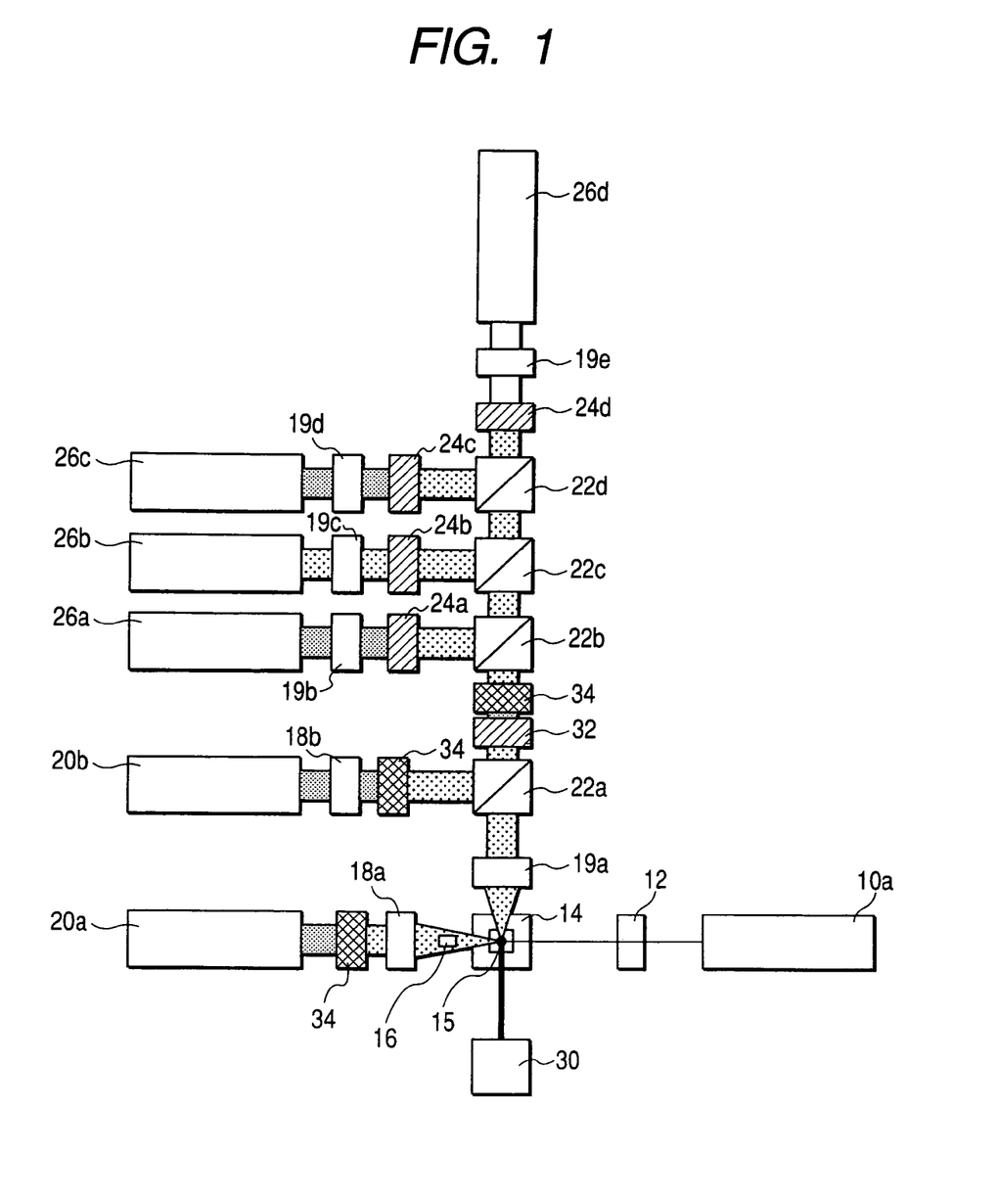
FIG. 1 is a schematic plan view of a flow cytometer according to a first embodiment of the invention.

FIG. 1 shows a flow cytometer according to a first embodiment of the invention. A laser light source 10a serves as a light source for scattered light excitation and irradiates the target particle 15 in the flow cell 14 with a laser beam by way of the beam shaping lens 12. Thus, the laser beam radiated at the target particle 15 excites forward scattered light and orthogonal scattered light respectively. Meanwhile, the flow cytometer is configured such that a laser beam directly incident on the flow cell 14 is blocked by a shade 16 disposed in front of the flow cell 14.

In this embodiment, as a light source for exciting fluorescence with respect to the target particle, a light-emitting diode (LED) 30 which can emit light in the blue-light region of relatively shorter wavelength is disposed. A light beam emitted from the LED 30 irradiates the target particle 15 in the flow cell 14, thereby exciting fluorescence.

Forward scattered light thus having been excited by the target particle 15 is condensed by the condenser lens 18a, input to the forward scattered light detector 20a after passing through a filter 34 for eliminating scattered light wavelength originating from the light source for exciting fluorescence constituted of the LED 30, and converted into an electric signal, In addition, the orthogonal scattered light and fluorescence having been excited by the target particle 15 are condensed by the condenser lens 19a, and caused to enter the serially-arranged beam splitters 22a, 22b, 22c, and 22d in sequence.

Here, first, the orthogonal scattered light is reflected by the beam splitter 22a. The thus-reflected light beam is condensed by the condenser lens 18b after passing through the filter 34 for eliminating scattered light wavelength originating from the light source for exciting fluorescence, input to the orthogonal scattered light detector 20b, and converted into an electric signal. Meanwhile, of fluorescence transmitted through the beam splitter 22a, a first fluorescence having been set in advance is reflected by the beam splitter 22b after passing through a filter 32 for eliminating the scattered light wavelength originating from the light source for scattered light excitation and the filter 34 for eliminating scattered light wavelength originating from the light source for exciting fluorescence. The reflected light beam is condensed by the condenser lens 19b after passing through the wavelength filter 24a, input to the fluorescence detector 26a, and converted into an electrical signal.

Of fluorescence transmitted through the beam splitter 22a, a second fluorescence having been set in advance is reflected by the beam splitter 22c. The reflected light beam is condensed by the condenser lens 19c after passing through the wavelength filter 24b, input to the fluorescence detector 26b, and converted into an electrical signal.

Similarly, of fluorescence transmitted through the beam splitter 22c, a third fluorescence having been set in advance is reflected by the beam splitter 22d. The reflected light beam is condensed by the condenser lens 19d after passing through the wavelength filter 24c, input to the fluorescence detector 26c, and converted into an electrical signal.

Thereafter, a transmitted light beam constituted of a fourth fluorescence having transmitted through the beam splitter 22d is condensed by the condenser lens 19e after passing through the wavelength filter 24d, input to the fluorescence detector 26d, and converted into an electrical signal.

In the configuration shown in FIG. 3, the reason for employing an argon laser as a light source for exciting fluorescence with respect to a target particle is that light in blue-light region of relatively shorter wavelength must be used as excitation light. Accordingly, by setting a light source constituted of an LED which can emit light in blue-light region as a light source for exciting fluorescence in addition to a conventional laser light source, the conventional laser light source can be used as a light source for scattered light excitation of the target particle, whereby a relatively inexpensive configuration for an apparatus can be realized. In addition, according to the configuration, analysis on scattered light and fluorescence with respect to the target particle can be attained more appropriately and efficiently.

In other words, since the light source 10a for scattered light excitation and the light source 30 for exciting fluorescence are provided independently with respect to the target particle 15, it is advantageous in being capable of selecting and detecting forward scattered light, orthogonal scattered light, and fluorescence excited by the respective light sources appropriately and reliably. In addition, the flow cytometer as a whole can be made simple and inexpensive configuration, but can be comprehensively applied to analysis of various target particles.

Figure 2:
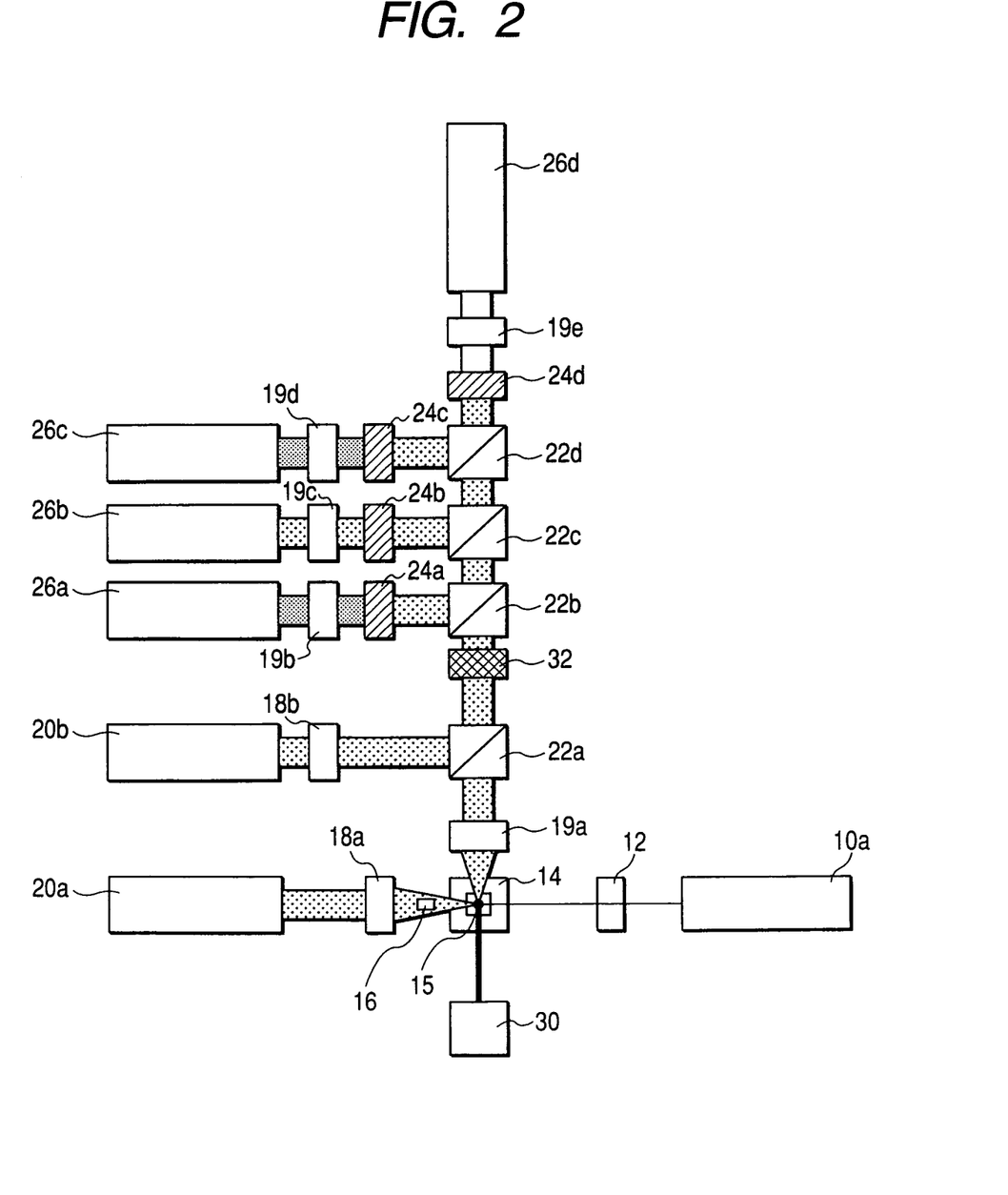
FIG. 2 is a schematic plan view of a flow cytometer according to a second embodiment of the invention.

FIG. 2 shows a flow cytometer according to a second embodiment of the invention. In this embodiment, the filters 34 which are disposed respectively between the forward scattered light detector 20a and the condenser lens 18a, between the beam splitter 22a and the condenser lens 18b of the orthogonal scattered light detector 20b, and between the beam splitter 22a and the filter 32 in the first embodiment are omitted. In other respects, the flow cytometer in this embodiment is completely analogous in configuration with the flow cytometer of the first embodiment.

Therefore, identical elements are denoted by the same reference numerals, and repetitive descriptions thereof are omitted. The flow cytometer having such a configuration can also perform the same functions as those of the flow cytometer of the first embodiment.

Next, a third embodiment of the invention will be described. A composite lens is obtained by integrating a plurality of lens elements having different focal points so as to form a single circular lens (cf., Japanese Patent Publication No. 11-23447A). It is possible to easily enhance sensitivity and S/N ratio in fluorescence detection by disposing such a composite lens on an optical path of scattered light, and appropriately disposing a plurality of fluorescence detectors at focal positions of the respective lens elements constituting the composite lens.

Figure 4:
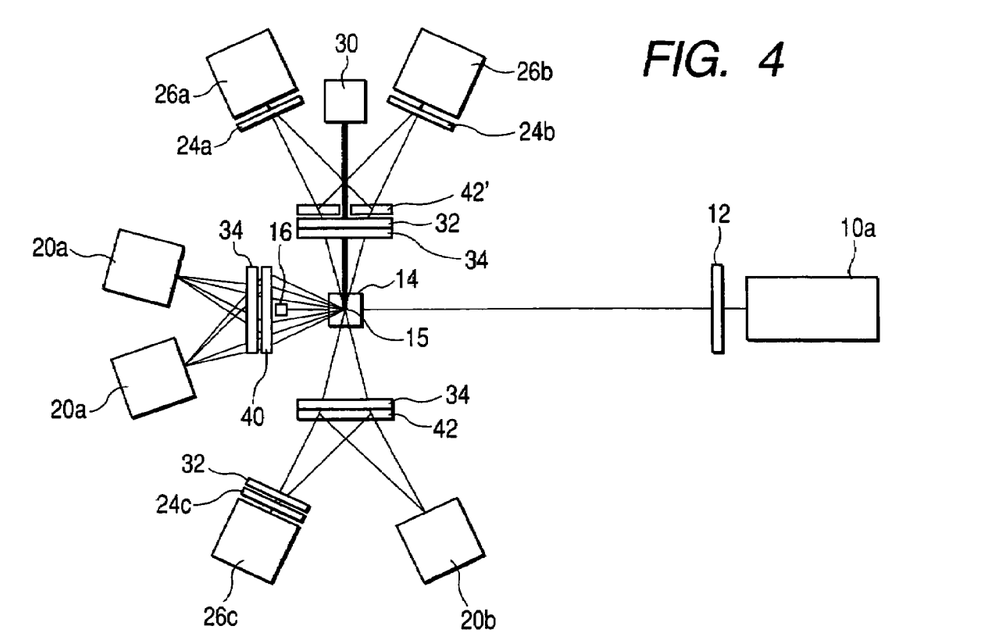
FIG. 4 is a schematic plan view of a flow cytometer according to a third embodiment of the invention.

FIG. 4 shows one example of such a configuration. Components similar to those in the first embodiment will be designated by the same reference numerals and repetitive explanations for those will be omitted. In this embodiment, composite lenses 40, 42a, and 42' are respectively applied to the forward scattered light detector 20a, the orthogonal scattered light detector 20b, and the fluorescence detectors 26a to 26c. More specifically, the condenser lens 18a for forward scattered light is replaced by the composite lens 40 in which a plurality of lens elements having different focal points are integrated concentrically to form a single circular lens (see FIGS. 10A to 10C). The forward scattered light detectors 20a are disposed at the respective focal points of the lens elements in the composite lens 40, and the filter 34 for eliminating scattered light wavelength originating from the light source for exciting fluorescence is disposed between the composite lens 40 and the detectors 20a.

Figure 11A:
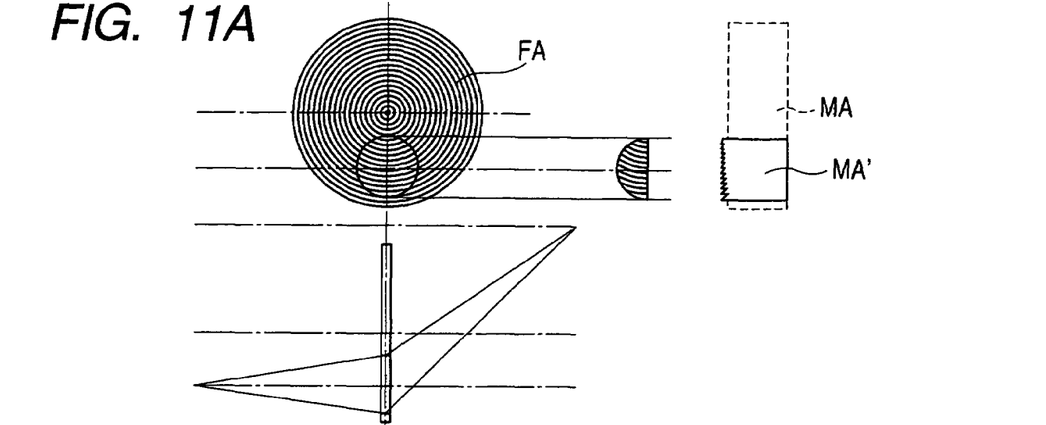
FIG. 11A to 11C show how to fabricate a composite lens 42 incorporated in the flow cytometers of the third, fourth sixth and seventh embodiments.
Figure 11B:
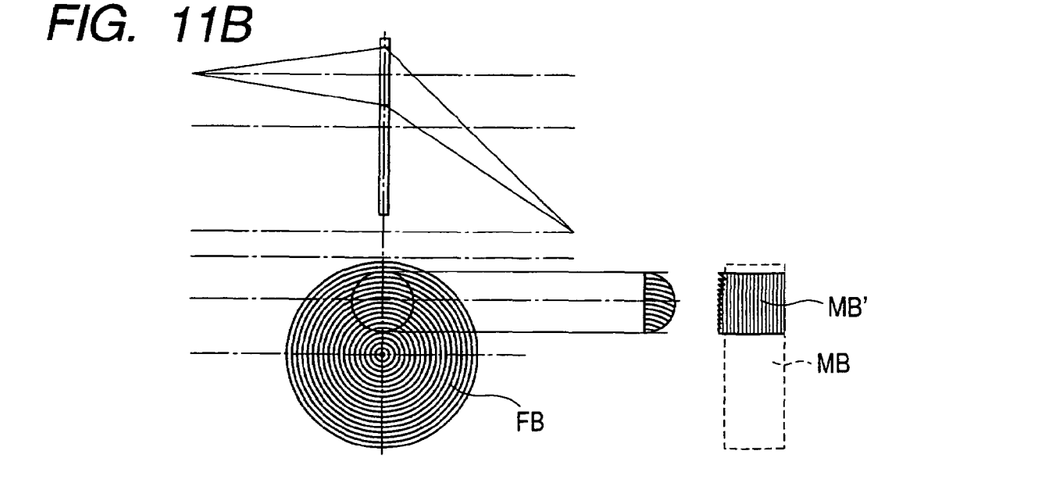
Figure 11C:
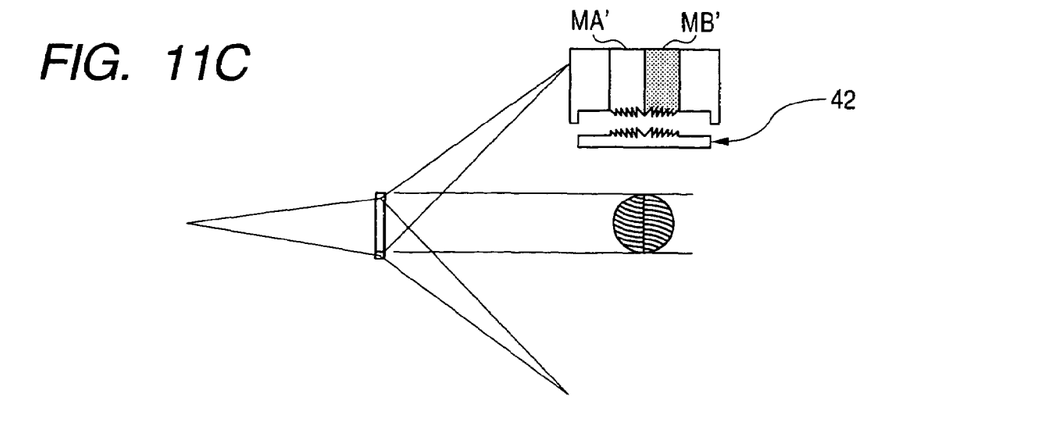

In addition, the condenser lens 19a for orthogonal scattered light and fluorescence, the beam splitter 22a and the orthogonal condenser lens 18b are replaced by the composite lens 42 in which a plurality of lens elements having different focal points are integrated concentrically to form a single circular lens (see FIGS. 11A to 11C). In addition, the condenser lenses 19b and 19c and the beam splitters 22b and 22c are replaced by the composite lens 42' in which a pinhole is formed on the composite lens 42. The composite lenses 42 and 42' are disposed at bilaterally symmetric positions of the incident light beam with respect to the flow cell 14.

In some cases, fluorescence is extremely weak as compared with scattered light, so that importance is placed on increase of sensitivity and S/N ratio in the fluorescence detection. More specifically, direct light from the light sources for exciting fluorescence and scattered light excitation are reflected, refracted, and scattered by a variety of optical devices and a flow cell. Such light (hereinafter referred to as "stray light") is extremely high in intensity as compared with fluorescence to be detected. Such stray light is brought incident on a detector by way of an optical path other than an intended optical path. Accordingly, as a method for eliminating the stray light and for increasing the S/N ratio and sensitivity in the fluorescence detection, elimination of the stray light by a pinhole is generally adopted.

In this case, a light beam is condensed by the composite lens 42 after passing through the filter 34 for eliminating scattered light wavelength originating from the light source for exciting fluorescence. The orthogonal, scattered light detector 20b is disposed at the focal point of one lens element in the composite lens 42. The fluorescence detector 26c is disposed at the focal point of the other lens element in the composite lens 42. The filter 32 for eliminating scattered light wavelength originating from the light source for scattered light excitation and the wavelength filter 24c is disposed between the detector 26c and the composite lens 42. With respect to the composite lens 42', a light beam is condensed by the composite lens 42' after passing through the filter 34 for eliminating scattered light wavelength originating from the light source for exciting fluorescence and the filter 32 for eliminating the scattered light wavelength originating from the light source for scattered light excitation. The fluorescence detectors 26a, 26b are disposed at each of the focal points of the lens elements in the composite lens 42'. The wavelength filter 24a, 24b are disposed between the composite lens 42' and the detectors 26a, 26b, respectively.

Further, in a case where the shade 16 is omitted and a condenser lens is instead disposed at an appropriate position between the flow cell 14 and the composite lens 40 or integrated with the composite lens 40, light absorbance of the target particles flowed within the flow cell 14 can be measured by a photo detector arranged on an optical axis of the light having passed through the condenser lens.

Figure 12A:
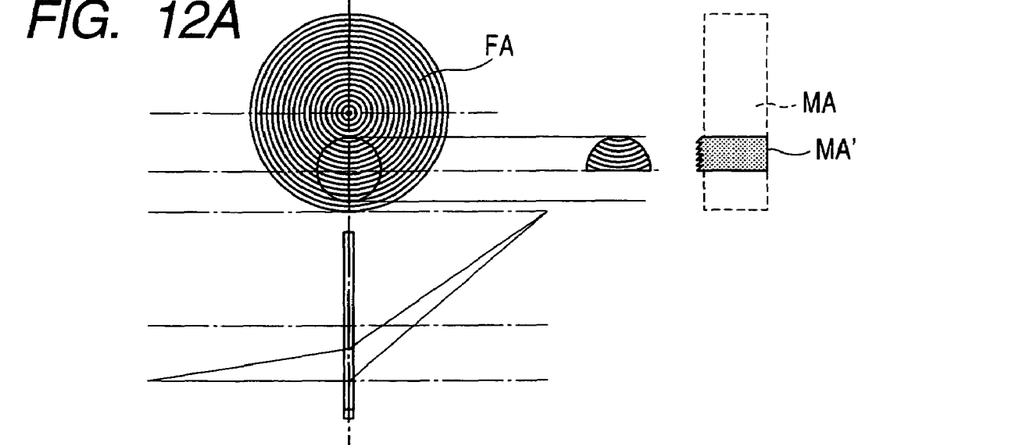
FIG. 12A to 12C show how to fabricate a composite lens 44 incorporated in the flow cytometers of the third and fourth embodiments.
Figure 12B:
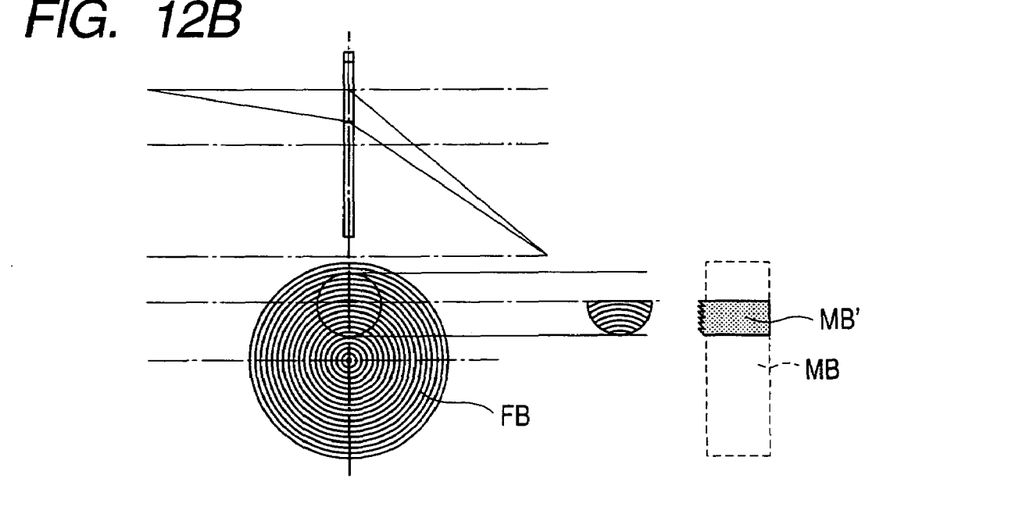
Figure 12C:
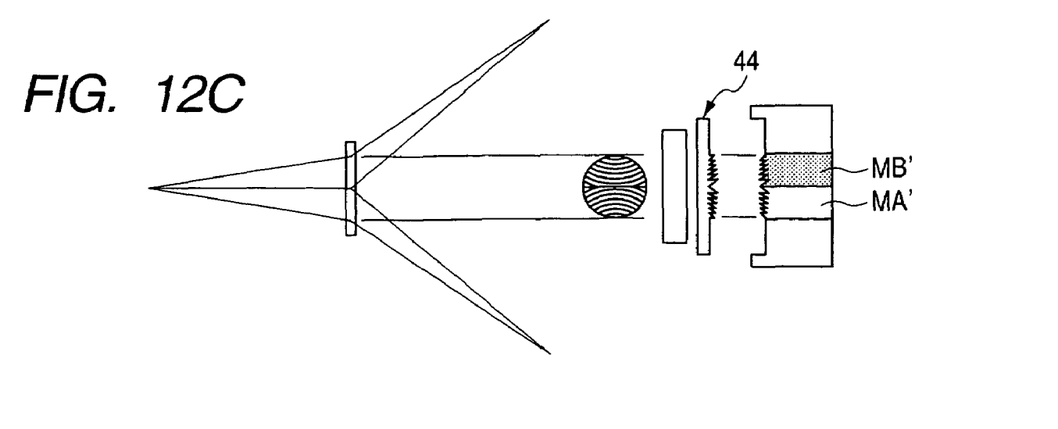
Figure 13A:
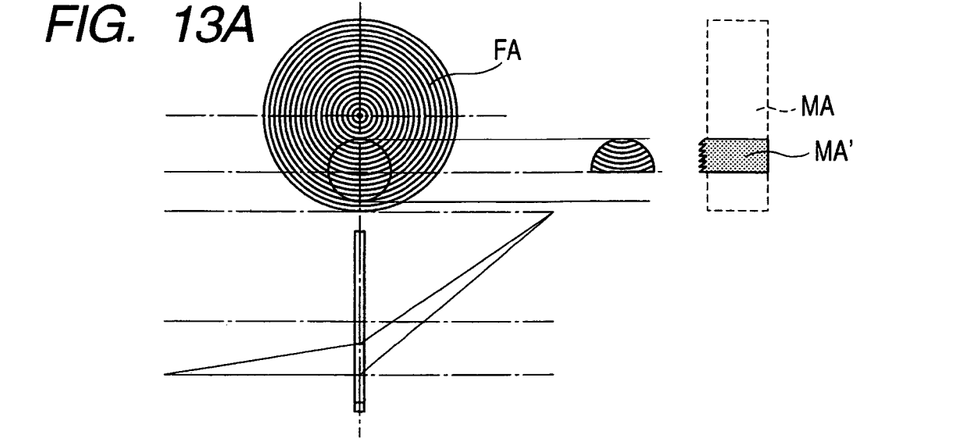
FIG. 13A to 13C show how to fabricate a composite lens 44' incorporated in the flow cytometers of the fifth embodiment
Figure 13B:
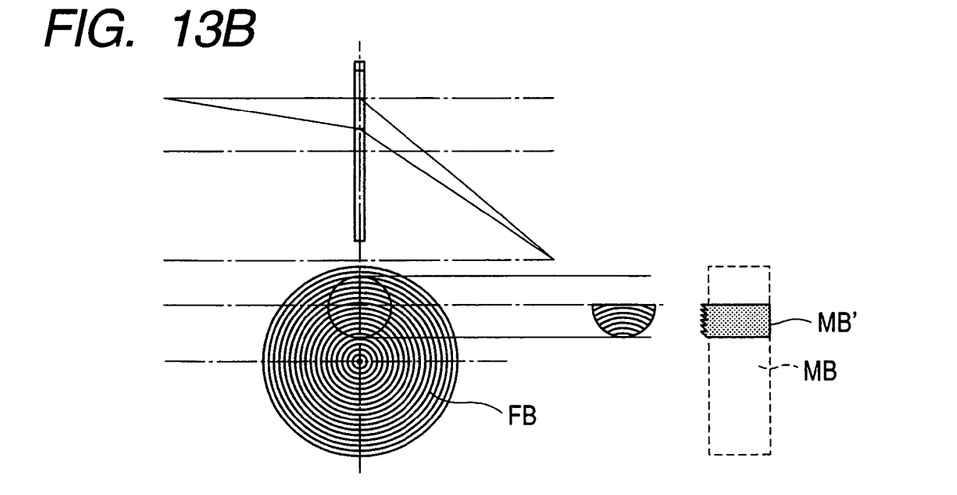
Figure 13C:
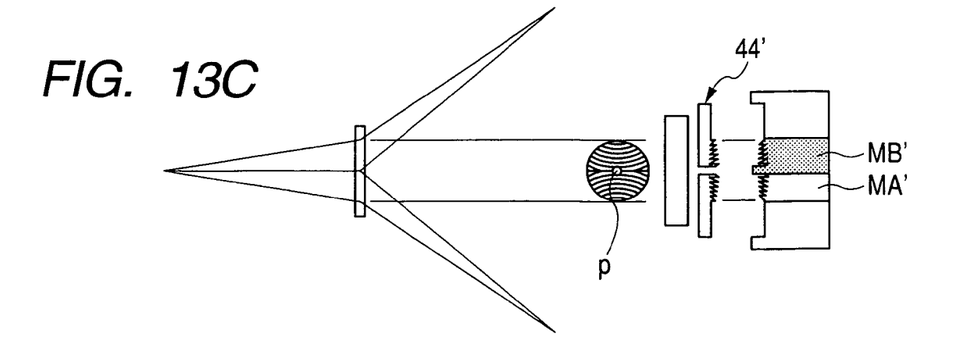

Here, the composite lens 42 and the composite lens 42' may be replaced with a composite lens 44 shown in FIGS. 12A to 12C or a composite lens 44' shown in FIGS. 13A to 13C, respectively.

Figure 5:
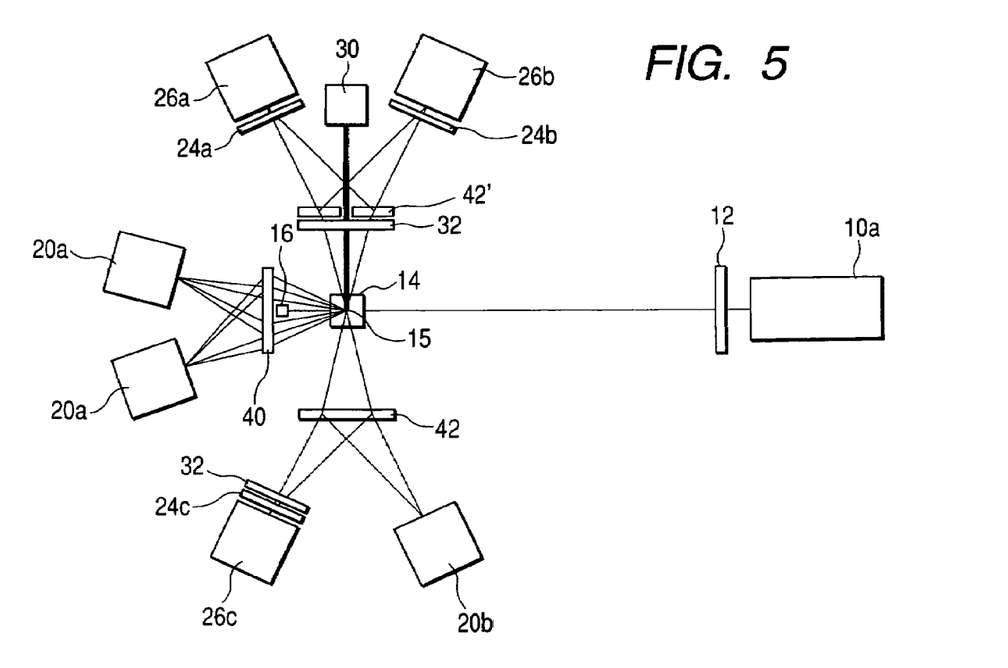
FIG. 5 is a schematic plan view of a flow cytometer according to a fourth embodiment of the invention.

FIG. 5 shows a fourth embodiment of the invention. Components similar to those in the third embodiment will be designated by the same reference numerals and repetitive explanations for those will be omitted. In this embodiment, the filters 34 which are disposed respectively between the forward scattered light detectors 20a and the composite lens 40, between the flow cell 14 and the composite lens 42, and between the flow cell 14 and the filter 32 in the third embodiment are omitted. The flow cytometer having such a configuration can also perform the same functions as those of the flow cytometer of the third embodiment.

Figure 6:
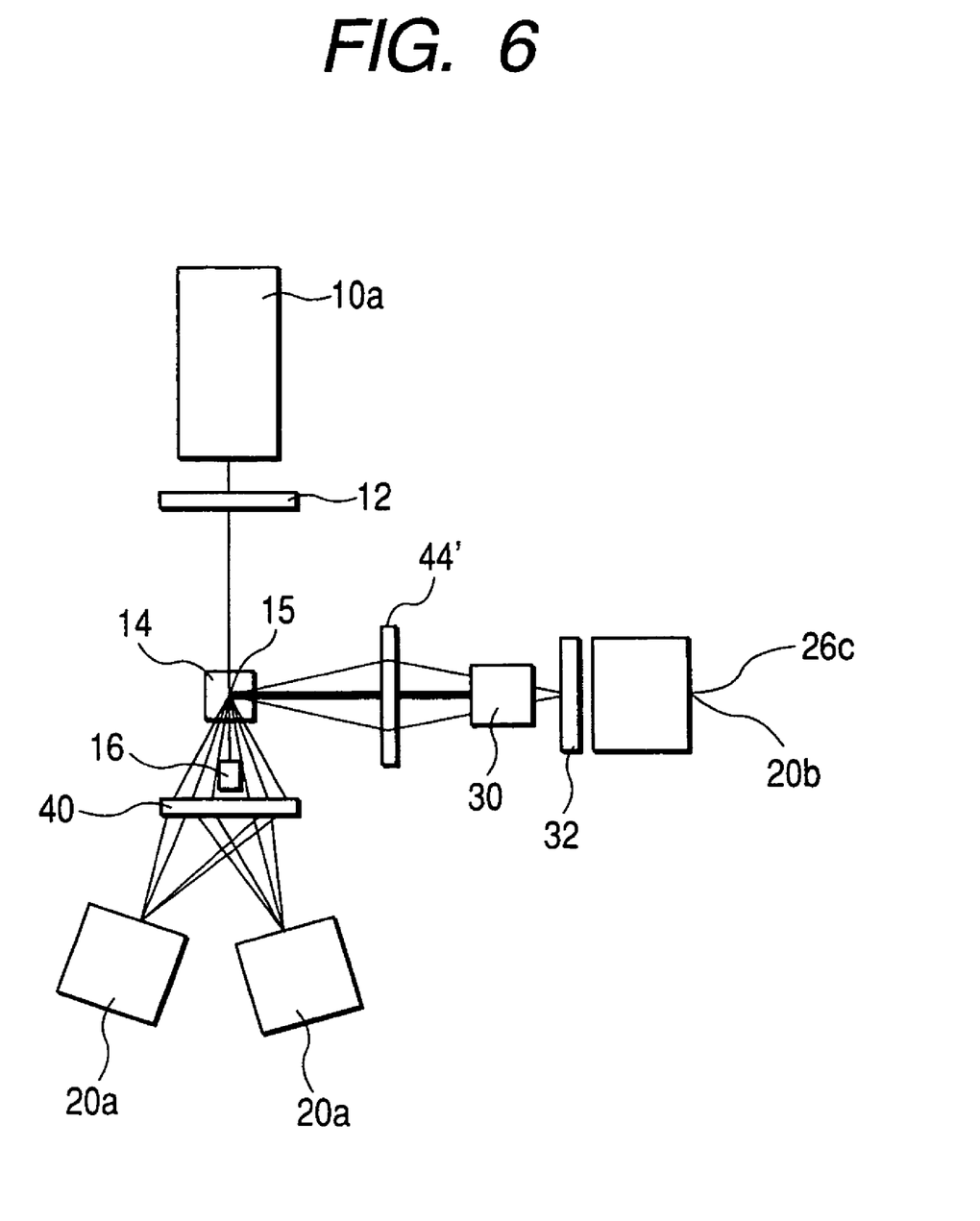
FIG. 6 is a schematic plan view of a flow cytometer according to a fifth embodiment of the invention.

FIG. 6 shows a fifth embodiment of the invention. Components similar to those in the fourth embodiment will be designated by the same reference numerals and repetitive explanations for those will be omitted. In this embodiment, the condenser lens 19a for orthogonal scattered light and fluorescence, the beam splitter 22a and the orthogonal condenser lens 18b shown in FIG. 1 are replaced by the composite lens 44' shown in FIGS. 13A to 13C.

Figure 7A:
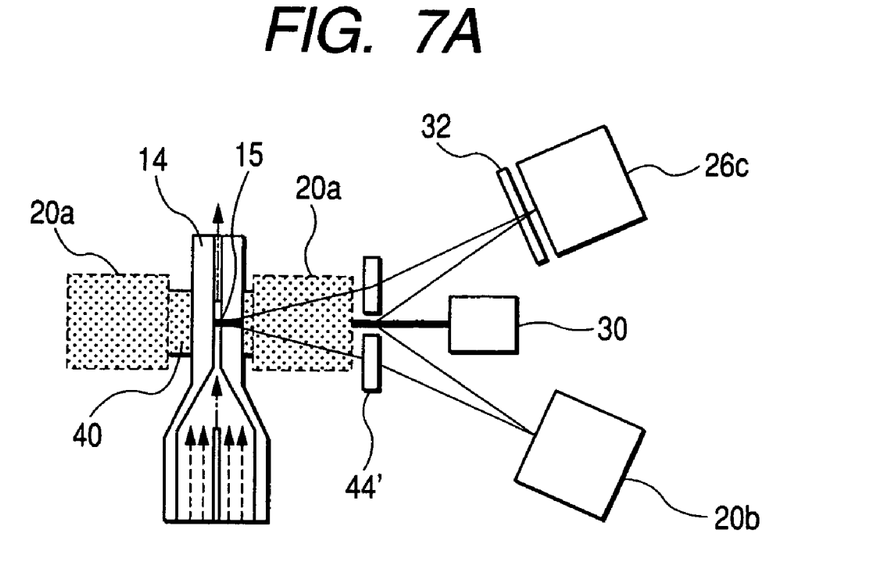
FIG. 7A is a schematic side view of the flow cytometer of FIG. 6.

Here, as shown in FIG. 7A, the orthogonal scattered light detector 20b is disposed at the focal point of one lens element in the composite lens 44', and the fluorescence detector 26c is disposed at the focal point of the other lens element in the composite lens 44'. The filter 32 for eliminating scattered light wavelength originating from the light source for scattered light excitation is disposed between the composite lens 44' and the detector 26c.

Figure 7B:
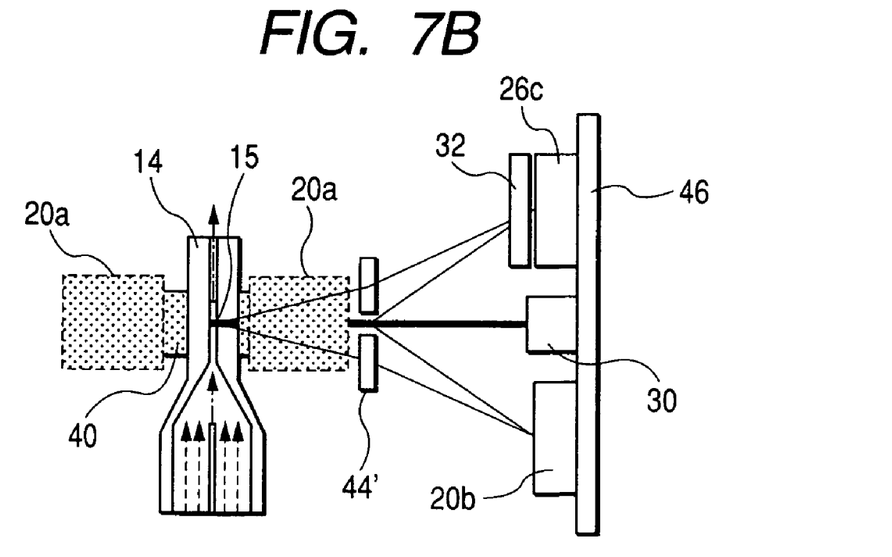
FIG. 7B is a schematic side view showing a case where an orthogonal scattered light detector and a fluorescence detector are mounted on a single board.

With the above configuration, as shown in FIG. 7B, the light source 30 for exciting fluorescence, the orthogonal scattered light detector 20b, and the fluorescence detector 26c can be disposed on a single board 46. Accordingly, decreases in the overall size and cost of the apparatus in overall size can be easily attained. In addition, the sensitivity and S/N ratio in the fluorescence detection can be enhanced when the target particle is analyzed with the fluorescence detection.

Figure 8:
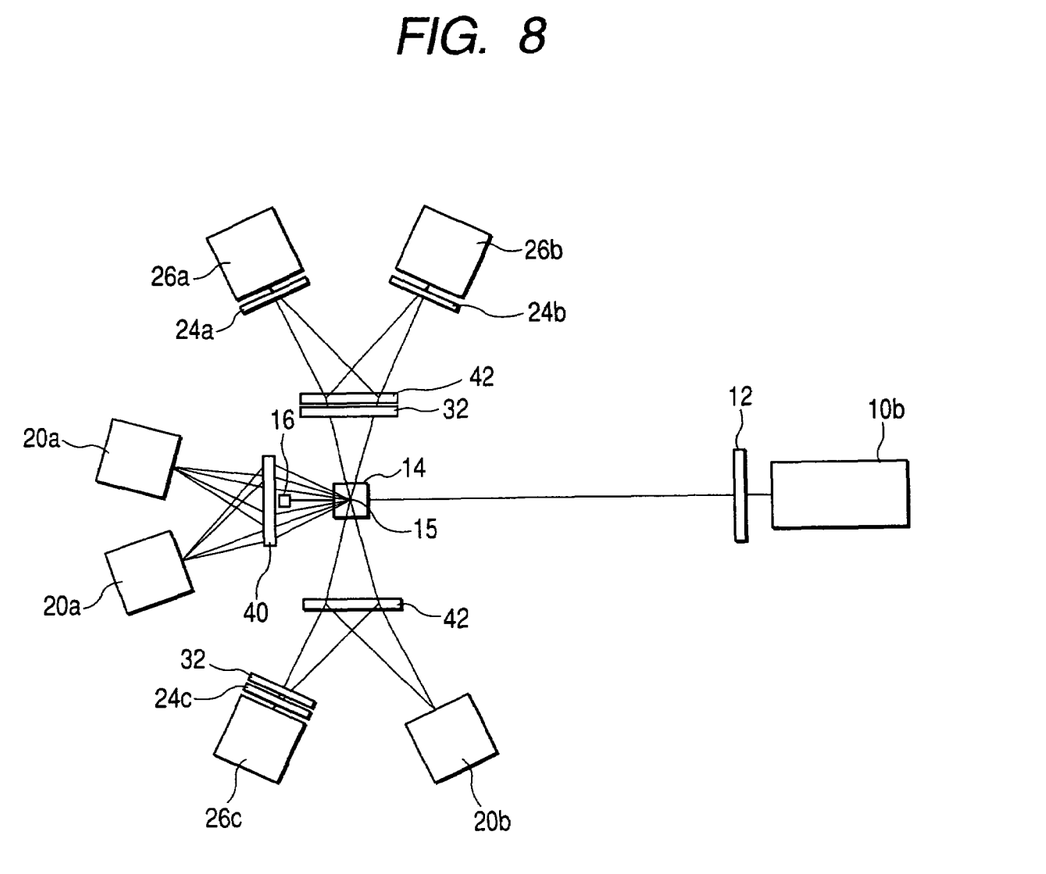
FIG. 8 is a schematic plan view of a flow cytometer according to a sixth embodiment of the invention.

FIG. 8 shows a sixth embodiment of the invention. Components similar to those in the fourth embodiment will be designated by the same reference numerals and repetitive explanations for those will be omitted In this embodiment, the argon laser 10b shown in FIG. 3 is used as a light source for exciting both of scattered light and fluorescence. Accordingly, the LED 30 for exciting fluorescence is omitted. The composite lens 42' shown in FIG. 5 is replaced by the composite lens 42 (this composite lens 42 is referred as a second composite lens while referring the composite lens 42 shown in FIG. 5 as a first composite lens 42), so that the first and second composite lenses 42 are disposed symmetrically with respect to the flow cell 14.

In this case, the orthogonal scattered light detector 20b is disposed at the focal point of one lens element in the first composite lens 42, and the fluorescence detector 26c is disposed at the focal point of the other lens element in the first composite lens 42. The filter 32 for eliminating scattered light wavelength originating from the light source for scattered light excitation and the wavelength filter 24c are disposed between the first composite lens 42 and the detector 26c. The light beam is condensed by the second composite lens 42 after passing through the filter 32 for eliminating scattered light wavelength originating from the light source for scattering light excitation. The fluorescence detectors 26a, 26b are disposed at the focal points of the lens elements in the second composite lens 42. The wavelength filter 24a, 24b are disposed between the second composite lens 42 and the detectors 26a, 26b, respectively.

Here, the composite lens 42 may be replaced with a composite lens 44 shown in FIGS. 12A to 12C or a composite lens 44' shown in FIGS. 13A to 13C, respectively.

Figure 9:
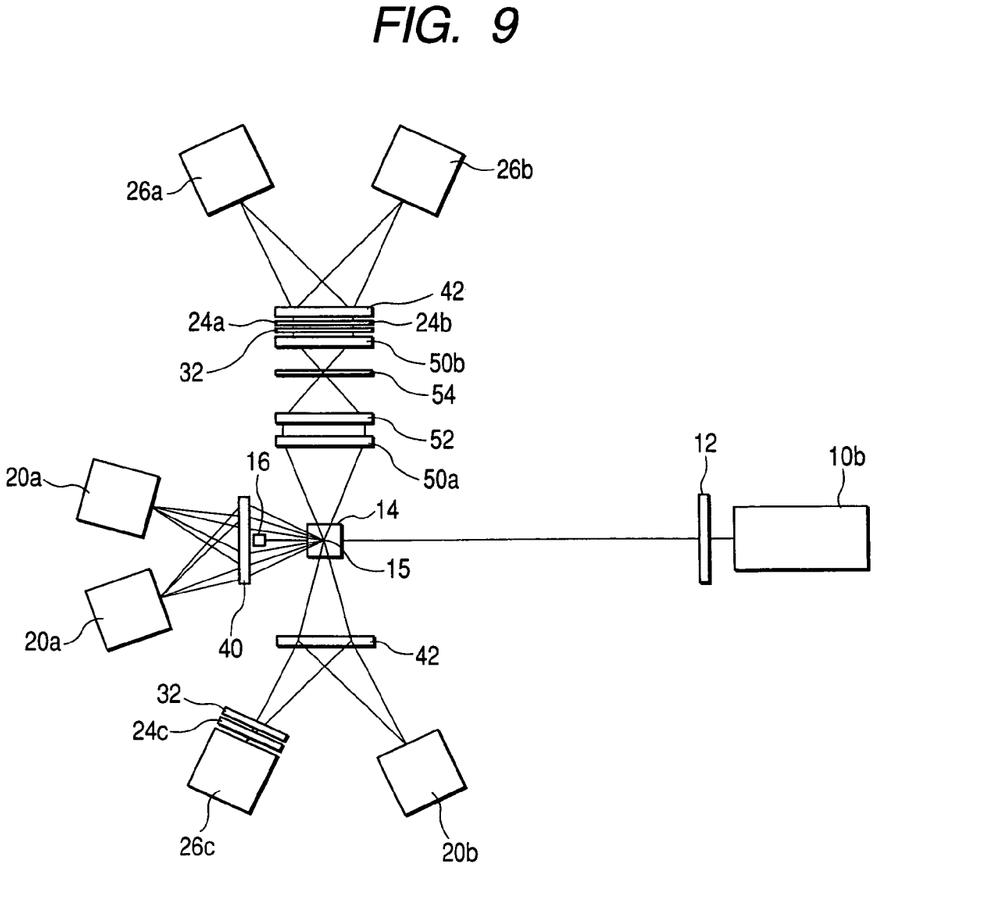
FIG. 9 is a schematic plan view of a flow cytometer according to a seventh embodiment of the invention.

FIG. 9 shows a seventh embodiment of the invention. Components similar to those in the sixth embodiment will be designated by the same reference numerals and repetitive explanations for those will be omitted. In this embodiment, the first composite lens 42 and the second composite lens 42 are disposed asymmetrically with respect to the flow cell 14. Specifically, the light beam is condensed by the second composite lens 42 after passing through an optical system comprising a collimator 50a, a condenser lens 52, a pinhole plate 54, a collimator 50b, and the filter 32 for eliminating scattered light wavelength originating from the light source for scattering light excitation. The wavelength filters 24a and 24b are disposed between the collimator 50b and the second composite lens 42.

The best condition for the wavelength filter disposed for obtaining fluorescence of a required selected wavelength is such that a light beam is perpendicularly incident on the filter. In other words, it is preferable that the wavelength filter is not so disposed that the light beam is incident thereon obliquely. With the above configuration, the wavelength filter can be used in its best condition by causing light, having been converted into parallel light with use of a collimator, to be brought incident to the wavelength filter perpendicularly.

Here, the composite lens 42 may be replaced with a composite lens 44 shown in FIGS. 12A to 12C or a composite lens 44' shown in FIGS. 13A to 13C, respectively.

Next, how to fabricate the composite lenses 40, 42, 42', 44, and 44' used in the flow cytometers of the third to seventh embodiments will be described.

Figure 10A:
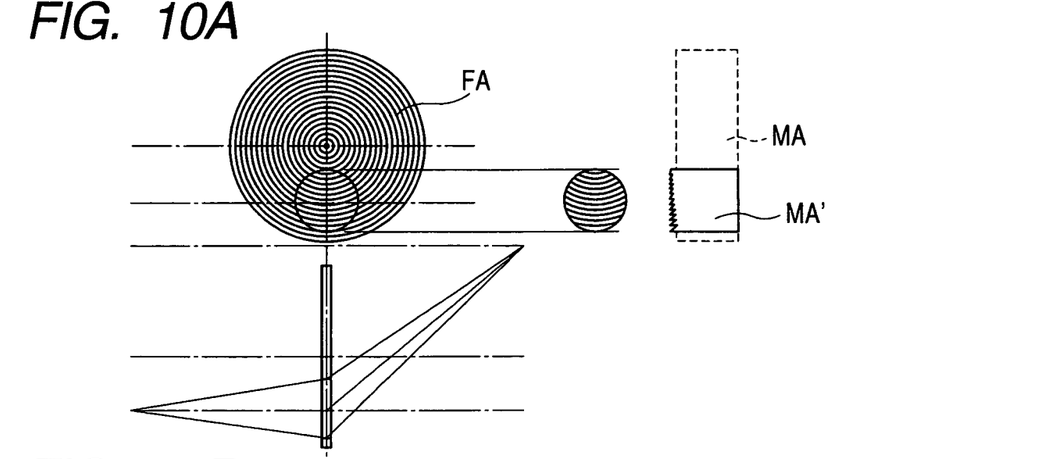
FIG. 10A to 10C show how to fabricate a composite lens 40 incorporated in the flow cytometers of the third to seventh embodiments.
Figure 10B:
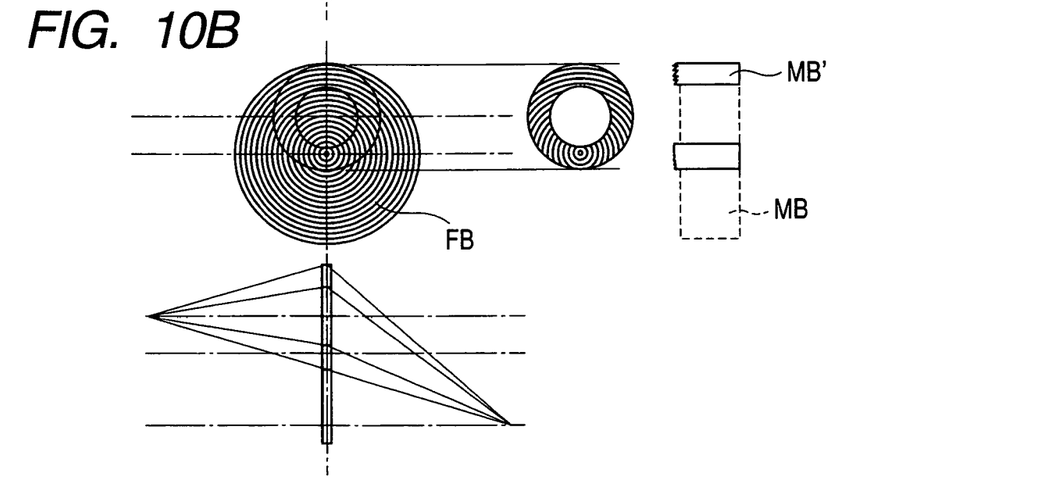
Figure 10C:
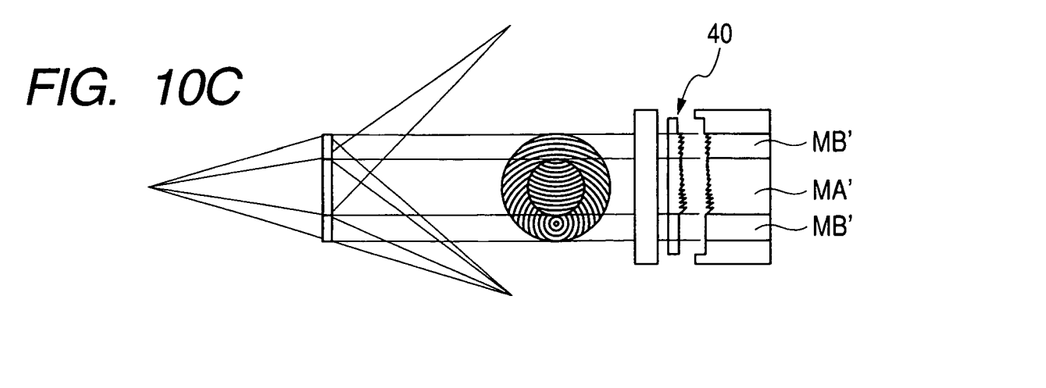

FIGS. 10A to 10C show how to fabricate the composite lens 40. A mold MA', serving as a first lens element, is formed by cutting or gouging a circular shape out of a mold MA for forming a Fresnel lens FA (see FIG. 10A). In addition, a mold MB', serving as a second element having a hole of a size into which the mold MA' can be inserted, is formed by cutting or gouging out from a mold MB for forming a Fresnel lens FB (see FIG. 10B). A single circular composite lens 40 having two focal points corresponding to the respective lens elements can be obtained by inserting the mold MA' into the hole of the mold MB' (see FIG. 10C). Here, the molds MA and MB may be identical; alternatively, the molds MA and MB may be molds for forming Fresnel lenses having different focal points or different principal axes.

FIGS. 11A to 11C show how to fabricate the composite lens 42. Specifically, a mold MA', serving as a first lens element, is formed by gouging or cutting a circular shape and is thereafter formed into a left-semicircular shape out of a mold MA for forming a Fresnel lens FA (see FIG. 11A). In contrast, a mold MB', serving as a second lens element, is formed by gouging or cutting a circular shape and is thereafter formed into a right-semicircular shape out of a mold MB for forming a Fresnel lens FB (see FIG. 11B). A single circular composite lens 42 having different focal points corresponding to the respective lens elements can be formed by coupling the mold MA' and the mold MB' (see FIG. 11C). In this case, the molds MA and MB may be identical; alternatively, the molds MA and MB may be molds for forming Fresnel lenses having different focal points or different principal axes.

FIGS. 12A to 12C show how to fabricate the composite lens 44. Specifically, a mold MA', serving as a first lens element, is formed by gouging or cutting a circular shape and is thereafter formed into an upper-semicircular shape out of a mold MA for forming a Fresnel lens FA (see FIG. 12A). In contrast, a mold MB', serving as a second lens element, is formed by gouging or cutting a circular shape and is thereafter formed into a lower-semicircular shape out of a mold MB or forming a Fresnel lens FB (see FIG. 12B). A single circular composite lens 44 having different focal points corresponding to the respective lens elements can be formed by coupling the mold MA' and the mold MB' (see FIG. 12C). In this case, the molds MA and MB may be identical; alternatively, the molds MA and MB may be molds for forming Fresnel lenses having different focal points or different principal axes.

FIGS. 13A to 13C show how to fabricate the composite lens 44'. It is basically identical with the method for fabricating the composite lens 44 except that a pinhole P is formed at a center portion of a composite lens 44 after coupling the mold MA' shown in FIG. 12A and the mold MB' shown in FIG. 12B.

Accordingly, although not illustrated in the drawings, a composite lens 42' can be obtained by forming a pinhole P at a center portion of the composite lens 42 shown in FIG. 11C after coupling the mold MA' shown in FIG. 11A and the mold MB' shown in FIG. 11B.

The preferred embodiments of the invention have hitherto respectively been described. However, it should be understood that the invention is not limited thereto, but may variously be modified and changed within the scope of the invention.

What is claimed is:

1. A flow cytometer, comprising:
   a laser light source, configured to emit a first light beam having a first spectrum width and irradiating a solution including target particles and being flowed in a flow cell to generate forward scattered light and orthogonal scattered light therefrom;
   a light emitting diode, configured to emit a second light beam having a second spectrum width broader than the first spectrum width and irradiating the solution in the flow cell to generate at least one wavelength of fluorescence therefrom;
   a first detector, adapted to detect the forward scattered light;
   a second detector, adapted to detect the orthogonal scattered light;
   at least one third detector, adapted to detect the at least one wavelength of fluorescence;
   a first filter, disposed between the flow cell and the third detector and adapted to eliminate scattered light generated from the target particles by the irradiation of the first light beam;
   a second filter, disposed between the flow cell and the first detector and adapted to eliminate scattered light generated from the target particles by the irradiation of the second light beam; and
   a third filter, disposed between the flow cell and the second detector and adapted to eliminate scattered light generated from the target particles by the irradiation of the second light beam.

2. The flow cytometer as set forth in claim 1, further comprising:
   a condenser lens; and
   a first beam splitter, wherein:
   the laser light source and the light emitting diode are so arranged that the orthogonal scattered light and the fluorescence are incident on the condenser lens; and the orthogonal scattered light and the fluorescence passed through the condenser lens are divided by the first beam splitter and respectively directed to the second detector and the third detector.

3. The flow cytometer as set forth in claim 2, wherein:

a plurality of third detectors, each of which includes a filter adapted to pass light having a wavelength corresponding to one of plural wavelengths of fluorescences, are provided; and the flow cytometer further comprises a second beam splitter adapted to divide the fluorescences passed through the first filter and directs each of the divided fluorescences to one of the third detectors.

4. A flow cytometer, comprising:

a light source, configured to emit a light beam irradiating a solution including target particles and being flowed in a flow cell to generate forward scattered light, orthogonal scattered light and at least one wavelength of fluorescence;

a first detector, adapted to detect the forward scattered light;

a second detector, adapted to detect the orthogonal scattered light;

at least one third detector, adapted to detect the at least one wavelength of fluorescence;

a first composite lens, having a plurality of focal points and arranged such that the orthogonal scattered light and the fluorescence are incident thereon without being subject to any reflection; and a lens, arranged such that the forward scattered light is incident thereon, wherein:

the second detector and the third detector are arranged at the respective focal points of the first composite lens.

5. The flow cytometer as set forth in claim 4, wherein the light source includes a laser light source which emits a first light beam for generating the forward scattered light and the orthogonal scattered light, and a light emitting diode which emits a second light beam for generating the at least one wavelength of fluorescence.

6. The flow cytometer as set forth in claim 4, wherein a plurality of lens elements, each of which has one of the focal points, are concentrically combined to form the first composite lens having a circular shape.

7. The flow cytometer as set forth in claim 4, wherein a plurality of semi-circular lens elements, each of which has one of the focal points, are combined to form the first composite lens having a circular shape.

8. The flow cytometer as set forth in claim 4, wherein:

a plurality of third detectors, each of which includes a filter adapted to selectively pass light having a wavelength corresponding to one of plural wavelengths of fluorescences, are provided;

the flow cytometer further comprises a second composite lens having a plurality of focal points and arranged at an opposite side of the flow cell to the first composite lens; and the third detectors are arranged at the respective focal points of the second composite lens.

9. The flow cytometer as set forth in claim 4, wherein the first composite lens is formed with a pinhole at a center portion thereof.

10. The flow cytometer as set forth in claim 8, wherein the second composite lens is formed with a pinhole at a center portion thereof.

11. The flow cytometer as set forth in claim 8, further comprising an optical system including a pair of collimators, a condenser lens and a member formed with a pinhole which are arranged between the collimators, the optical system being arranged between the flow cell and at least one of the first composite lens and the second composite lens.

12. The flow cytometer as set forth in claim 4, further comprising a fourth detector, adapted to measure light absorbance of the target particles.

13. The flow cytometer as set forth in claim 4, further compromising a filter, disposed between the flow cell and the third detector, and adapted to selectively pass light having a wavelength corresponding to the wavelength of the fluorescence.

* * * * *